United States Patent [19]

Khoo

[11] 4,087,742

[45] May 2, 1978

[54] HOT WATER HEATER CORROSION DETECTOR PROBE

[75] Inventor: Sian W. Khoo, Etobicoke, Canada

[73] Assignee: Canadian Gas Research Institute, Don Mills, Canada

[21] Appl. No.: 597,864

[22] Filed: Jul. 21, 1975

[51] Int. Cl.² ............................................. G01N 27/42
[52] U.S. Cl. ....................................... 324/29; 204/148; 204/197; 324/65 CR
[58] Field of Search ...................... 324/29, 71 R, 30 R, 324/65 CR; 204/195 C, 147, 148, 196, 197

[56] References Cited

U.S. PATENT DOCUMENTS

| | | | |
|---|---|---|---|
| 2,869,003 | 1/1959 | Marsh et al. | 204/195 C |
| 3,037,920 | 6/1962 | Vixler | 324/29 |
| 3,867,274 | 2/1975 | Herman | 204/148 |

Primary Examiner—Rudolph V. Rolinec
Assistant Examiner—Michael J. Tokar
Attorney, Agent, or Firm—Arne I. Fors

[57] ABSTRACT

A method and apparatus for providing a continuous indication of the interior condition of a water heater tank are shown herein. Iron interior surface of water heater tank is normally protected from corrosion by cathodic protection with the provision of a sacrificial anode element made of a highly anodic metal. A zinc probe is incorporated in the water heater tank such that the potential measured between the zinc probe and the iron interior surface indicates the condition of the sacrificial anode element thus providing an indication of the effectiveness of the cathodic protection. The zinc probe may be conveniently incorporated in the drain cork of the water heater tank.

10 Claims, 3 Drawing Figures

HOT WATER HEATER CORROSION DETECTOR PROBE

BACKGROUND OF THE INVENTION

This invention relates to a method and apparatus for providing a continuous indication of the interior condition of an enclosed fluid container such as a water heater tank having a cathodic corrosion protection means therein.

Containers for fluid such as water heater tanks commonly have a steel housing to provide an enclosed chamber for holding the fluid. The interior surface of such steel housing is subject to corrosion due to contact with the fluid. In order to prevent the corrosion usually the interior surface is lined with a corrosion resistant material such as glass. However, even in such glass lined housing, there is still some bare iron surface which is exposed to the fluid in the container.

The bare iron interior surface in a glass lined or unlined water heater tank is subject to a corrosive action manifested by the existence of a galvanic electromotive force generated between different points on the iron surface and the free ions in the water. The iron surface is anodic with respect to the water; this causes the iron to dissolve gradually. Such corrosion of the iron interior surface of the water heater tank can be prevented by mounting in the tank a metal element which is strongly anodic with respect to all the bare iron surface. The anodic metal element is electrically connected to the iron interior surface so that it forms a cell with the iron surface and the water serves as the electrolyte of such cell. The iron interior surface becomes cathodic with respect to the metal element and the anodic metal element will dissolve in the process instead of the iron interior surface. Such anodic metal element is referred to as a sacrificial anode because it is sacrificed in the process such that there is no corrosion of the iron interior surface. Magnesium may be used as a sacrificial anode in water heater tanks because it does not release any toxic material into the water in the process.

Since the sacrificial anode is depleted in the cathodic protection process, it is essential to inspect it from time to time to see if it has been depleted to an unsatisfactory state or if it has depleted completely or there is such an excess amount of liming in the tank that the cathodic protection process is no longer in operation. Liming is the deposition or accumulation of a layer of hard calcareous material in the tank. However, as water heater tanks all have a fully enclosed structure, visual inspection of the sacrificial anode and the interior of the tank is not possible. Removal of the sacrificial anode for inspection may not be safely or conveniently made by the user since the anode must be mounted carefully and the temperature and pressure in the tank are hazardous if proper precautions are not adopted in removing the anode. Furthermore, the frequency of the removal of the anode for inspection may not be easily established as it varies according to variable conditions such as the mineral content in the water supply in a particular district and the rate of water flow according to the amount of water used by the user.

PURPOSE OF THE INVENTION

It is the principal object of the present invention to provide a method and apparatus which provides a continuous indication of the corrosion conditions within an enclosed fluid container having a sacrificial anode therein for preventing corrosion of said container.

It is an object of the present invention to provide a reference probe means which may be removably mounted on a water heater tank for providing en electrical measurement which is indicative of the corrosion conditions within an enclosed water heater tank having a sacrificial anode therein.

It is another object of the present invention to provide a means for indicating the liming condition of an enclosed water heater tank.

It is a further object of the present invention to provide a means for measuring the frequency of water withdrawals from an enclosed water heater tank.

BRIEF DESCRIPTION OF DRAWINGS

These and other objects of this invention together with its advantages will be more apparent from the following description and drawings which illustrate a specific embodiment by way of example and in which.

DESCRIPTION OF SPECIFIC EMBODIMENT

Figure 1:
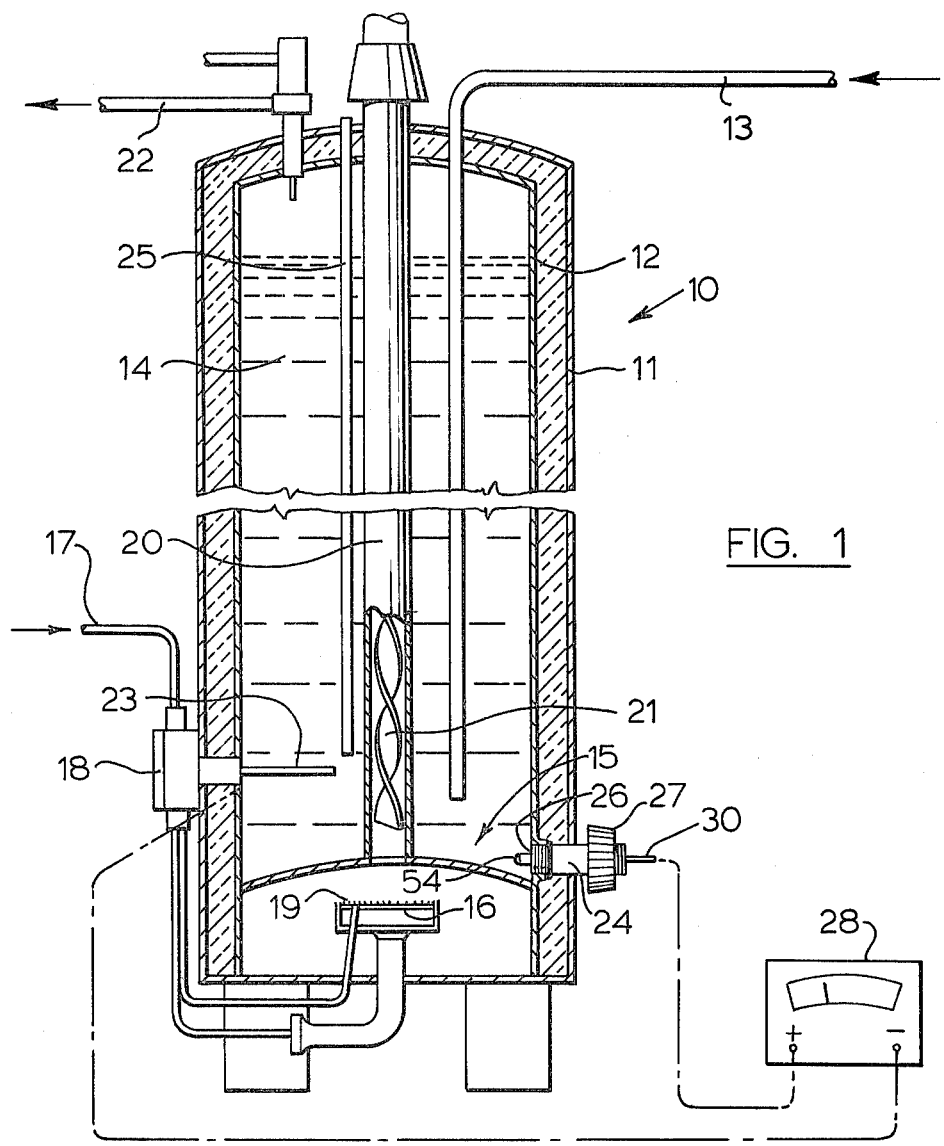
FIG. 1 is a schematic side elevation view of a water heater tank having a reference probe means according to the present invention.

Referring to the drawings, a gas fired hot water tank 10 is shown. A gas fired hot water tank is shown as an example of the present invention. It will be apparent to one skilled in the art that similar structures may be incorporated in electrically or oil operated hot water tanks. The tank has an enclosed steel housing 11, the interior surface 12 of which may be lined with a corrosion resistant material such as glass. Usually, in such glass lined water heater tank, many bare iron surfaces still exist such as the iron surface of inlet and outlet water pipe couplings, defects in the glass lining, and, for simplicity of illustration, the interior surface 12 herein is an unlined bare iron surface.

Water is supplied to the tank through inlet pipe 13 and the volume of water 14 in the tank is heated by a heat transfer surface 15 provided in the tank. The heat transfer surface 15 as shown in this specific embodiment is heated by a gas burner 16. Gas is supplied to the burner 16 through gas supply conduit 17 and a thermostatic controller 18. The gas is also supplied to a pilot burner 19. The burnt gas is exhausted through a flue 20 having a flue baffle 21. The hot water is withdrawn from the tank through outlet pipe 22.

The temperature of the water 14 in the tank is detected by temperature sensing means 23 and the signal from the temperature sensing means 23 is fed to the thermostatic control 18 which controls the supply of the gas to the heating device 15 or the actuation of the electric heating elements in an electric hot water tank.

The water heater tank 10 is commonly provided with a drain pipe 24 located at the side and close to the bottom of the tank so that the water in the tank may be completely drained if required.

A sacrificial anode element 25 is mounted in the tank in order to provide cathodic protection to the iron interior surface 12. The sacrificial anode element may be in the form of an iron or copper core coated with a layer of highly anodic metal such as zinc, magnesium, aluminium or an alloy of such highly anodic metals. The sacrificial anode element 25 must be mounted in direct electrical contact with the iron interior surface 12. As shown in FIG. 1, the top end of the sacrificial anode element is in direct electrical contact with the iron interior surface 12. Due to the electrical contact between the sacrificial anode element and the interior surface and the presence of water 14 which serves as an electrolyte, a current will flow from the higher potential anode element through the water to the iron interior surface. This natural electrochemical process will provide a cathodic protection to the iron interior surface 12. The magnesium layer on the anode element will be depleted in the process to form a magnesium salt which is dissolved in the water. No corrosion will occur in the iron interior surface since it is cathodic with respect to the water 14 as well as the sacrificial anode element 25.

The effectiveness of the cathodic protection is proportional to the amount of current flowing from the sacrificial anode to the iron interior surface through the water. The current decreases as the amount of anodic metal of the sacrificial anode is gradually depleted in the process. It also decreases due to the accumulating liming deposit which physically insulates the anodic metal from the water. Thus, by measuring this current a continuous indication of the condition of the sacrificial anode may be obtained. According to the present invention, this current is indirectly measured by measuring the voltage between the water and the iron interior surface. The voltage measurement is made by connecting the negative terminal of a voltmeter to the iron interior surface and connecting its positive terminal to the water. The connection to the iron interior surface may be made at any convenient location such as through the thermostatic controller 18. The connection to the water is made through a reference probe means 26 incorporated in the drain cock 27 which is mounted at the drain pipe 24. The reference probe means 26 is electrically insulated such that it has no direct electrical contact with the iron interior surface. In this manner, there is no electrochemical action between the reference probe means and the iron interior surface, and the reference probe means merely provides an electrical connection from the water to the positive terminal of the voltmeter. It is found that typically a voltage potential measurement of more negative than about +0.3 volt obtained between the reference probe and the iron interior surface indicates that adequate cathodic protection is provided by the sacrificial anode element to the iron interior surface. When the anode element has deteriorated to an unsatisfactory state, the potential measurement will become more positive than about +0.3 volt.

The potential may be measured by a high resistance voltmeter 28 or other sensitive potential measuring devices which can provide voltage readings in the millivolt range such as a potentiometer so as to avoid polarization errors caused by current flowing through the measurement circuit. Thus, the voltmeter provides a continuous visual indication of the efficiency of the cathodic protection provided by the sacrificial anode element without having to remove the anode element from the tank or to cut open the tank for inspection. Other suitable devices may be incorporated to provide a visual light signal or sound signal when the potential is more positive than positive 0.3 volt.

Furthermore, since the liming deposit on the reference probe means is similar to the liming deposit on the interior surface on the tank as well as the surface of the sacrificial anode element, the reference probe means may be conveniently removed to provide an indication of the degree of liming accumulation in the tank.

The reference probe means is preferably made of a metal which does not release any harmful or toxic material into the water and does not form corrosion products of variable composition which could interfere with the potential to be measured. The corrosion products will make the measured potential erratic. Zinc or stainless steel may be used for such purpose.

Figure 2:
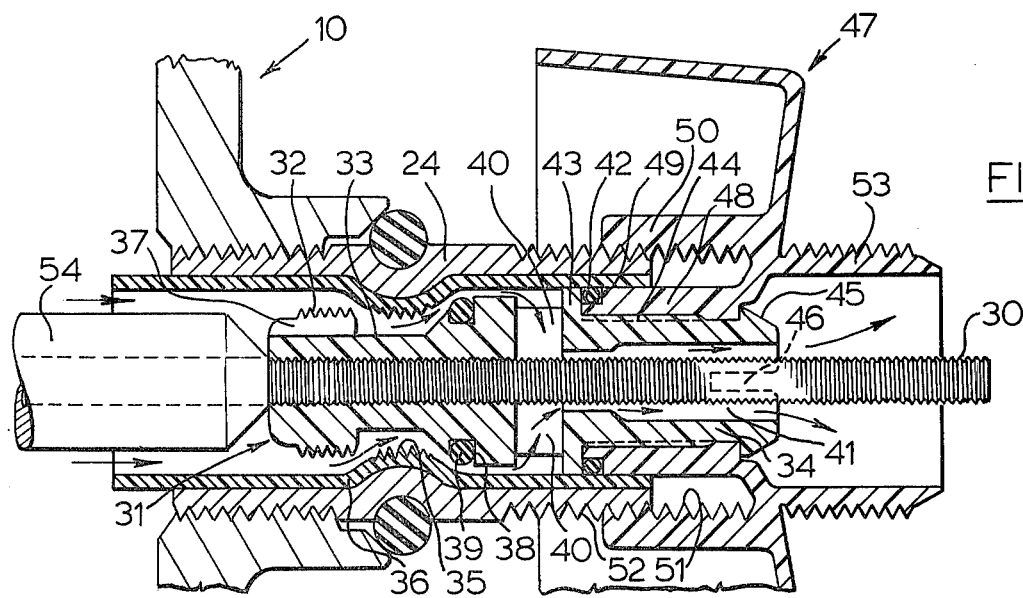
FIG. 2 is a sectional side view of water heater tank drain cock incorporating the reference probe means according to the present invention.
Figure 3:
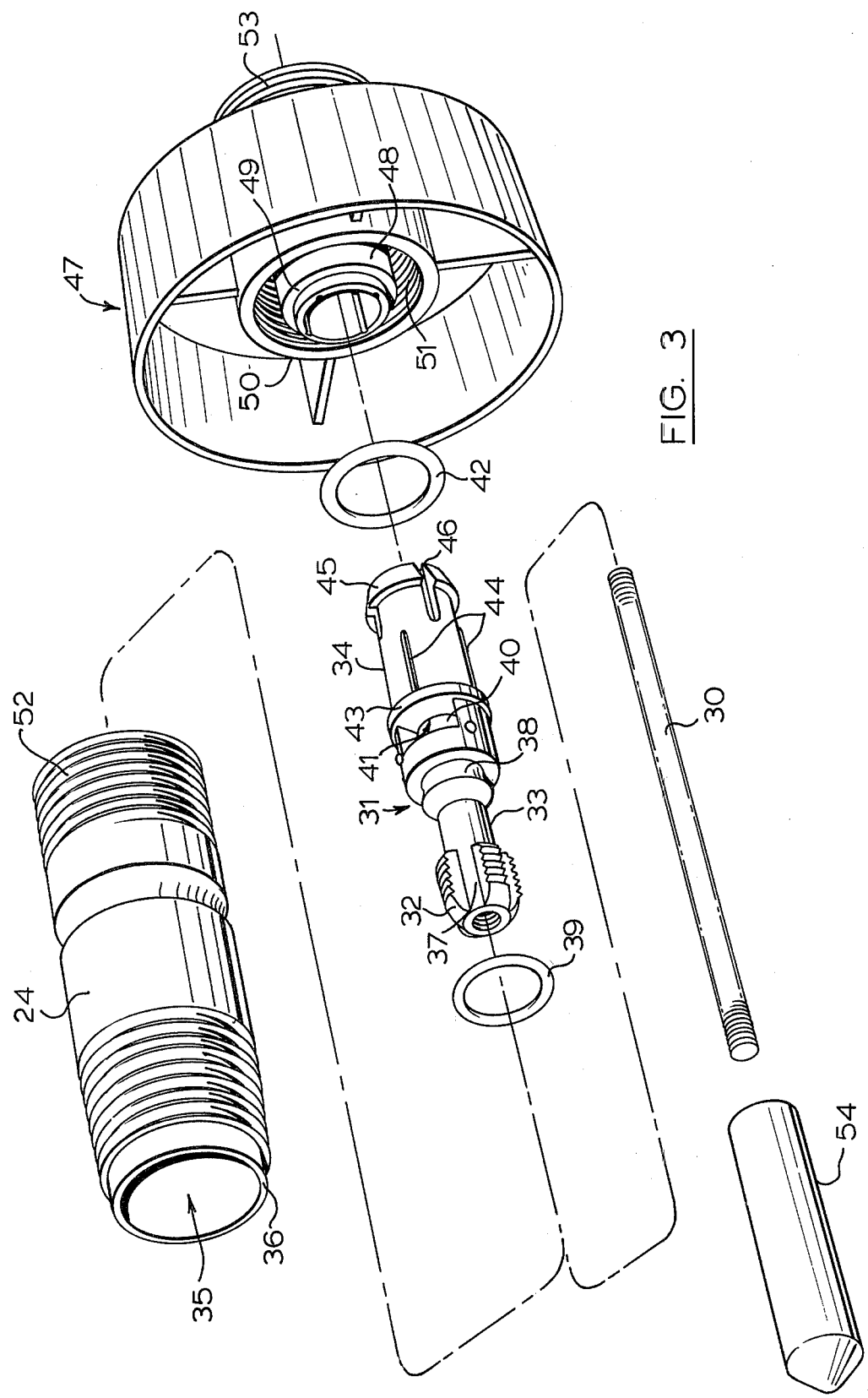
FIG. 3 is an exploded perspective view showing the component parts of the drain cock reference probe arrangement of FIG. 2.

FIGS. 2 and 3 show a specific embodiment of the reference probe means incorporated in a drain cock of known design. The reference probe means 26 is a zinc rod. One end of the rod is mounted over a copper rod or core 30 which is threadingly mounted to a substantially cylindrical drain cock body 31 made of an electrically insulating material such as polyvinyl chloride plastics or hard rubber. The cylindrical cock body 31 has a threaded cylindrical portion 32, a narrow neck portion 33 and a cylindrical tubular portion 34. The threaded surface of the threaded cylindrical portion 32 is engageable with a threaded collar 35 provided in a plastic electrically insulated lining 36 formed on the interior surface of the drain pipe 24. A plurality of longitudinal channels 37 are formed on the threaded cylindrical portion 32. The cylindrical tubular portion 34 has a circular groove 38 formed at its junction with the neck portion for receiving an O-ring 39 to be mounted thereon.

At least two ports 40 are formed on the tubular portion 34. The ports 40 communicate with the center longitudinal cavity 41 of the tubular portion. A second 0-ring 42 is mounted on the tubular portion and positioned against a collar 43 immediately adjacent to the ports 40. Four longitudinal ridges 44 are formed on the tubular portion 34 and an expanded end portion 45 is formed at its free end. The end portion 45 has a bevelled surface slanting outwards toward the longitudinal axis of the cylindrical body 31. A plurality of slits 46 are formed in the end portion 45 such that it is resiliently flexible radially with respect to the longitudinal axis of the cylindrical body.

The cylindrical body 31 is mounted on a cap-like cover member 47 which has a central sleeve portion 48. The tubular portion 34 of the cylindrical body 31 may be snugly mounted in this central sleeve portion as best shown in FIG. 2. The radial resiliency of the end portion of the cylindrical body 31 and the bevelled surface of the end portion 45 facilitate the insertion of the tubular portion 34 into the central sleeve portion 48. The O-ring 42 will be held in a groove 49 formed between the collar 44 of the tubular portion 34 and the sleeve portion 48. The inside wall of the sleeve portion has a plurality of longitudinal grooves which engage with the ridges 44 to prevent any relative rotational movements between the cylindrical body 31 and the cover body 47.

The central sleeve 48 is surrounded by a spaced concentric threaded sleeve 50. The threads 51 of the threaded sleeve are engageable with the threads 52 of the drain pipe 24 of the tank for mounting the drain cock thereon. A threaded coupling tube 53 is provided on the drain cock for connection to a conventional hose for conducting the water to a drain during the draining operation.

As best shown in FIG. 2, the copper rod 30 extends throughout the entire length of the cylindrical body 31. A short end portion of the copper rod 30 extends beyond the end of the threaded cylindrical portion 32 for mounting the zinc rod 54 thereon. The short end portion of the copper end will be completely covered by the zinc rod such that the copper rod is not exposed to the water in the tank. The other end portion of the copper rod 30 extends through the center of the tubular portion 34 of the cylindrical body and the coupling tube 53 for electrical connection to the voltmeter 28.

The threads on the threaded cylindrical portion 32 of the cylindrical body 31 and the threads on the threaded collar 35 of the drain pipe 14 are left-handed, while the threads 51 and 52 on the threaded sleeve 48 and the drain pipe 24 are right-handed. The drain cock is mounted on the drain pipe by rotating the cover body 47 counterclockwise such that the threaded cylindrical portion 32 engages with the collar 35. As soon as the threaded cylindrical portion 32 is drawn past the collar 35, the threaded sleeve 50 may be engaged with the drain pipe 24 by rotating the cover body clockwise. The O-ring 42 will snugly engage with the inside wall of the drain pipe to prevent water from passing between the cylindrical body 31 and the drain pipe 24. The drain cock may be tightened by continuing rotating the cover body clockwise so that the O-ring 39 will press tightly against the collar 35 to close the drain pipe.

In the draining operation, the drain cock is loosened by rotating the cover body 47 counterclockwise until the O-ring 39 is spaced from the collar 35 such that the drain pipe is opened, as shown in FIG. 2. The water as shown by the arrows will flow out of the tank through the space between the neck portion 33 and the drain pipe 24 then through the ports 40 and the cavity 41 to the coupling tube 53. The channels 37 on the threaded cylindrical portion 32 of the cylindrical body 31 facilitate the water to flow more freely to the space between the cylindrical body and the drain pipe.

The potential measurements provided between the reference probe means and the iron interior surface of the tank is also affected by the rate of water flow through the water heater tank. Thus, the potential measurements may also be utilized to monitor the water withdrawal from the tank.

While the invention has been particularly shown and described with reference to a preferred embodiment thereof, it will be understood by those skilled in the art that various changes in form and detail may be made therein without departing from the spirit and scope of the invention.

What I claim as new and desire to protect by Letters Patent of the United States is:

1. A hot water heater tank comprising an enclosed chamber having a substantially exposed iron interior surface, sacrificial anode means disposed in said chamber and in electrical contact with said iron interior surface operative to provide an electro-chemical cathodic protection to said iron interior surface, an elongated non-sacrificial metal element formed of zinc or stainless steel mounted to said tank and being electrically insulated from said iron interior surface and extending into said chamber and operatively in contact with the water in said chamber whereby an electromotive force measurable between said metal element and said iron interior surface is indicative of the efficiency of the cathodic protection.

2. In a hot water heater tank having an enclosed chamber with a substantially exposed iron interior surface and sacrificial anode means disposed in said chamber and in electrical contact with said iron interior surface to provide an electrochemical cathodic protection to the latter, a drain outlet means operative for draining water from said chamber, a drain cock means removably mounted in said drain outlet means and being operative to close or open said drain outlet means, an elongated non-sacrificial metal element mounted in said drain cock means and extending into said chamber to contact the water therein, said metal element being electrically insulated from said iron interior surface whereby an electromotive force measurable between said metal element and said iron interior surface is indicative of the efficiency of the cathodic protection.

3. A hot water heater tank according to claim 2, wherein said sacrificial anode means is chosen from the group consisting of magnesium and aluminum, and said metal element is chosen from the group consisting of zinc and stainless steel.

4. A method of measuring the efficiency of cathodic protection to iron interior surface of an enclosed hot water heater tank by sacrificial anode means disposed in said tank, comprising mounting a non-sacrificial metal element to said tank, said metal element being electrically insulated from said iron interior surface and operatively in contact with the water in said tank, measuring electrical electrochemical potentials manifested between said metal element and said iron interior surface whereby the measured potentials more negative than a predetermined threshold value indicate said cathodic protection being efficiently in operation.

5. A method according to claim 4, wherein said metal element is incorporated in a drain cock means in a drain outlet means of said hot water heater tank.

6. A method according to claim 5, wherein said electrochemical potentials are measured by a high resistance voltage measurement device connected to said metal element and said iron interior surface.

7. A method according to claim 6, wherein said threshold value is positive 0.3 volt.

8. A drain cock device removably securable in a drain outlet pipe of a hot water heater tank, comprising a substantially cylindrical body threadingly engageable in said drain outlet pipe and operative selectively to open or close said drain outlet pipe, a metal rod element mounted in said cylindrical body and having a threaded end portion therein, a zinc probe element securable to and covering over said threaded end portion of said metal rod whereby when said cylindrical body is mounted in said drain outlet pipe said zinc probe element extends into said tank, the other end portion of said metal rod extending outward of said cylindrical body to provide an electrical connection terminal.

9. A drain cock device according to claim 8, wherein said metal rod is an elongated copper rod.

10. A drain cock device according to claim 9, wherein said copper rod has a threaded longitudinal surface, and said cylindrical body has a threaded central longitudinal bore adapted to receive said copper rod to be threadingly secured therein.

* * * * *